(12) United States Patent
Kawaji

(10) Patent No.: US 7,276,641 B2
(45) Date of Patent: Oct. 2, 2007

(54) EXTERNAL PLASTER CONTAINING 4-BIPHENYLACETIC ACID

(75) Inventor: Toshikuni Kawaji, Ohkawa-gun (JP)

(73) Assignee: Teikoku Seiyaku Co., Ltd., Kagawa (JP)

( * ) Notice: Subject to any disclaimer, the term of this patent is extended or adjusted under 35 U.S.C. 154(b) by 0 days.

(21) Appl. No.: 11/218,568

(22) Filed: Sep. 6, 2005

(65) Prior Publication Data

US 2006/0015054 A1 Jan. 19, 2006

Related U.S. Application Data

(63) Continuation of application No. 10/203,276, filed as application No. PCT/JP00/08440 on Nov. 29, 2000, now abandoned.

(51) Int. Cl.
*A61F 13/00* (2006.01)
*C08L 9/06* (2006.01)

(52) U.S. Cl. ............ 602/48; 524/10; 524/502; 524/575; 424/447; 424/448

(58) Field of Classification Search ............ 602/41–43, 602/48, 52; 424/443–449; 524/575, 502, 524/10
See application file for complete search history.

(56) References Cited

U.S. PATENT DOCUMENTS 4,398,985 A * 8/1983 Eagon .................. 156/233
6,471,984 B1 * 10/2002 Hirashima et al. .......... 424/443
6,946,514 B2 * 9/2005 Kawaji ...................... 524/575

FOREIGN PATENT DOCUMENTS

| JP | 53-074537 | | 7/1978 |
| JP | 5374537 | * | 7/1978 |
| JP | 54-101420 | | 8/1979 |
| JP | 56-39014 | | 4/1981 |
| JP | 60-2253 | | 1/1985 |
| JP | 4-321624 | | 11/1992 |
| JP | 5-105630 | | 4/1993 |
| JP | 6-24969 | | 2/1994 |

* cited by examiner

*Primary Examiner*—Kim M. Lewis
(74) *Attorney, Agent, or Firm*—Crowell & Moring LLP

(57) ABSTRACT

An aqueous hot melted type adhesive base material containing 4-biphenylyl acetic acid (BPAA) is provided. The adhesive base material contains constant amounts of BPAA and has good drug releasability, so that bioavailability of the drug is enhanced. An analgesic and anti-inflammatory external plaster containing BPAA is also provided. The plaster is obtained by dissolving BPAA into an aqueous hot melted type adhesive base material comprising as essential components a styrene-isoprene-styrene block copolymer, an adhesive resin, an antioxidant, lanolin, and water.

23 Claims, No Drawings

EXTERNAL PLASTER CONTAINING 4-BIPHENYLACETIC ACID

CROSS REFERENCE TO RELATED APPLICATIONS

This application is a continuation of patent application Ser. No. 10/203,276, filed Aug. 8, 2002, which is a national phase of International Patent Application No. PCT/JP00/08440, filed Nov. 29, 2000.

TECHNICAL FIELD

The present invention relates to plasters containing 4-biphenylyl acetic acid (general name: FELBINAC; hereinafter simply referred as to "BPAA"), and more particularly, to analgesic and anti-inflammatory external plasters in which BPAA is dissolved into an aqueous hot melted type adhesive base material comprising a styrene-isoprene-styrene block copolymer, an adhesive resin, an antioxidant, lanolin, and water as essential components.

BACKGROUND ART

BPAA is a pharmacologically active agent that is widely used in various external preparations, such as ointments, lotions, and aqueous plasters (cataplasm), for the purposes of relieving pain and alleviating inflammation in various disease conditions, including osteoarthritis, muscle- and fascia-related lumbago, periarthritis humeroscapularis, tendinitis, tenosynovitis, peritendinitis, external humeral epicondylitis (such as tennis elbow), sore muscle, and post-traumatic swelling and pain.

Among these external preparations, ointments and lotions have been considered less suitable for administration of BPAA continuously and in constant dosages and are also thought to be inconvenient since they may stick elsewhere other than the intended application site, and may sometimes soil the clothes at the time of administration. On the other hand, an aqueous plaster, though not associated with these problems, has a low adhesiveness and thus requires fixing means such as a strip of surgical tape so that it stays on flextion parts such as elbows and knees.

Non-aqueous adhesives are also known, including those that use natural or synthetic rubber as a base material and plasters that make use of adhesive base material using acrylate adhesive base. This type of plaster has a strong adhesiveness and is thought to overcome the drawbacks of aqueous plasters. Thus, much effort has been put into development of external preparations of various drugs using such plasters.

However, the low solubility of BPAA makes it difficult to dissolve BPAA directly in adhesive base material. BPAA is readily soluble in dimethylacetamide, less soluble in acetone, ethanol, glacial acetic acid, and ether, and hardly soluble in water. BPAA is also hardly soluble in polyols, glycols, and esters, which are commonly used as a solvent for drugs in preparation of external plasters.

For this reason, attempts have been made to use various solubilizers to dissolve BPAA For example, Japanese Patent Laid-Open Publication No. Hei 4-321624 discloses a technique in which crotamiton is used as a solubilizer for BPAA. Nonetheless, the use of crotamiton as a solubilizer to help dissolve BPAA has achieved a solubility of at most about 7%. Also, the solubility achieved by the aforementioned aqueous plaster, which uses diisopropanolamine as the solubilizer, is not more than about 11%. Thus, it has been difficult heretofore, even with the help of a solubilizer; to obtain a hot melted type adhesive base material that contains BPAA in an amount sufficient to allow it to exert desired pharmacological effects.

In aqueous plasters containing BPAA, BPAA is solubilized by first dissolving diisopropanolamine in water so that it becomes ionized and then adding BPAA to the solution, thus facilitating dissolving of BPAA in the solution. Though possible, adoption of this technique in producing non-aqueous adhesives containing BPAA, for example, solvent adhesives, which require a drying process, or hot melted type adhesive base materials, which require exposure to high temperature, may result in evaporation of moisture and thus crystallization of BPAA in the adhesive base.

A surfactant may also be used as a component of the hot melted type adhesive base material in order to facilitate mixing of water. This approach, however, may cause skin irritation and thus is not favorable.

Aside from the above-described approaches, a water-absorbable or water-soluble high molecular compound is thought to enable the adhesive material to absorb water. One disadvantage of this approach is that moisture evaporates when the temperature is raised to melt the successive adhesive in continuous production. As a result, the high molecular compound crystallizes and forms unwanted particles in the adhesive base. Moreover, water is surrounded by the high molecular compound which is presented in the adhesive base material, and this prevents diffusion of BPAA in the adhesive preparation, and as a result, the efficiency of drug utilization is lowered Accordingly, it is an objective of the present invention to provide an aqueous hot melted type adhesive base material containing BPAA that overcomes the above-identified problems. This adhesive base material contains constant amounts of BPAA and exhibits a good releasability of the drug from the adhesive, thereby enhancing bioavailability of the drug.

SUMMARY OF THE INVENTION

The present invention has been devised to overcome the above-described problems and provides in one aspect an analgesic and anti-inflammatory external plaster containing 4-biphenylyl acetic acid as active ingredient, wherein 4-biphenylyl acetic acid is dissolved into an aqueous hot melted type adhesive base material comprising styrene-isoprene-styrene block copolymer, an adhesive resin, an antioxidant, lanolin, and water as essential components of said adhesive base material.

More specifically, the present invention provides an analgesic and anti-inflammatory external plaster containing BPAA, obtainable through the process comprising the steps of melting and kneading a styrene-isoprene-styrene block copolymer, an adhesive resin, an antioxidant, lanolin, and a softener to form an adhesive base material; adding water and an aqueous solution of BPAA to the adhesive base material at a temperature of 80 to 100° C., while stirring, to form an adhesive base material containing BPAA; coating said base material on a liner, laminating the liner to a backing; and cutting the resulting backing to a desired size.

In one preferred embodiment of the present invention, the analgesic and anti-inflammatory plaster for external use containing BPAA contains water in an amount of 0.1 to 30%.

In a further aspect, the present invention provides an analgesic and anti-inflammatory external plaster containing BPAA in which BPAA is dissolved into the above-described aqueous hot melted type adhesive base material in a stable manner.

In summary, what is characteristic of the present invention resides in the use of the aqueous hot melted type adhesive base material that contains a styrene-isoprene-styrene block copolymer, an adhesive resin, an antioxidant, lanolin and water as essential components. The plaster obtained by dissolving BPAA in such aqueous hot melted type adhesive base material has an enhanced drug stability as well as an enhanced drug releasability over time and thus overcomes the aforementioned drawbacks of the conventional art.

BEST MODE FOR CARRYING OUT THE INVENTION

An external plaster in accordance with the present invention will now be described in detail with the emphasis on the types and the amounts of the components contained.

Styrene-isoprene-styrene block copolymer (hereinafter referred simply as to "SIS") for use in the plaster of the present invention is synthetic rubber to form the basic component of the adhesive base material and has ratio of styrene/rubber as 14/86. While adhesive base materials containing SIS are normally produced by melting at temperatures of 120 to 160° C., it is essential to design the production process of the aqueous hot melted type adhesive base material of the present invention so that the components are kneaded and mixed at 80 to 100° C. in order to permit mixing of water.

It is thus preferred that the amount of SIS to be used is from 10 to 30% (as measured in % by weight with respect to the total weight of the adhesive preparation containing BPAA. All of the numbers expressed in percentages appear in the following description are calculated in the same manner.), more preferably from 15 to 25%. If the amount is less than 10%, the cohesion of the adhesive material is lost and it tends to remain on the surface to which it is applied after the plaster has been removed. In comparison, if the amount exceeds 30%, the adhesive base material becomes hard, making kneading and mixing of the adhesive base material difficult. As a result, the adhesion of the base material is reduced.

Adhesion resin for use in the plaster of the present invention may be any of the following resin materials: aromatic resins such as Petrosin® (manufactured by MITSUI PETROCHEMICAL INDUSTRIES, Ltd.) and Hiresin® (manufactured by TOHO OIL Co., Ltd.); aliphatic resins such as Escorez® (manufactured by TONEN OIL Co., LTD.) and Quintone® (manufactured by NIPPON ZEON Corporation); alicyclic petroleum resins; rosin resins; rosin ester resins; and terpene resins.

The amount of the adhesive resin to be used is preferably from 15 to 35%, and more preferably from 20 to 30%. If the amount is less than 15%, then the adhesive base material can hardly exhibit the adhesion, and the cohesion of the adhesive base material is reduced. As a result, the base material tends to remain on the surface to which it is applied after the plaster has been removed. In comparison, if the amount exceeds 35%, the adhesive base material becomes hand, making kneading and mixing of the adhesive difficult. As a result, the adhesiveness of the base material is reduced.

Antioxidant for use in the plaster of the present invention is contained for the purpose of preventing the adhesive base material from undergoing deterioration due to oxidation during mixing and storage of the adhesive base material. Examples of the antioxidant include dibutylhydroxytoluene, pentaerythrityl-tetrakis[3-(3,54-t-butylhydroxyphenyl)]propionate, and tocopherol acetate. Preferably, these antioxidants are added in an amount of 0.1 to 2%.

Lanolin for use in the plaster of the present invention is also called "wool fat" and is purified and collected when secretions of sheep are washed off of wool. Lanolin is a cholesterin fat that does not lose its ointment-like viscosity even when added with 2 to 3 times as much water and is readily soluble in ether, chloroform petroleum, benzine, or the like.

What is characteristic of the plaster of the present invention resides in the use of lanolin as a component of the adhesive base material for the plaster. Lanoline is blended to serve not only to retain moisture in the adhesive base material but also as a softener of the adhesive base material.

The amount of lanolin to be used is determined based on the balance between the amount of water and the amounts of other oils and fats and the softeners such as liquid rubbers. Preferably, the amount of lanolin is from 5 to 40% and more preferably from 10 to 30%. Lanolin contained in an amount less than 5% is insufficient for stable retention of water, whereas when contained in an amount greater than 40%, it makes the adhesive base material unfavorably sticky.

Water is contained for the purposes of dissolving BPAA and providing the base material with a sense of "cooling effect". The amount of water is determined based on the balance between the amount of the active ingredient and the amount of lanolin and is preferably from 0.1 to 30% and more preferably from 0.3 to 20%. If the amount of water is less than 0.1%, it becomes difficult not only to dissolve BPAA in the base material but also to provide the "cooling effect" to the plaster. In comparison, the adhesive preparation can hardly have required properties if the amount of water exceeds 30%.

The plaster of the present invention may optionally contain a solubilizer for BPAA, including amines and crotamiton Examples of amine include monoethanolamine, diethanolamine, diisopropanolamine, triethanolamine, and triisopropanolamine. The amount of amine to be contained is preferably in the range from 1 to 15%.

In addition, the plaster of the present invention may further contain a softener for the purpose of providing the adhesive base material with a proper plasticity. Aside from the above-described lanolin component, examples of the softener include liquid rubbers, liquid paraffin, and fatty acid esters including isopropyl myristate. The amount of the softener to be used is preferably from 5 to 50% and more preferably from 10 to 45%.

Less than 5% of the softener is insufficient to provide sufficient plasticity to the adhesive base material. In such a case, the base material becomes too hard to be spread. In comparison, the softener, if contained in an amount exceeding 50%, makes the adhesive base material unfavorably sticky and brings about unfavorable situations such as the base material remaining on the surface to which it is applied after the plaster has been removed, or the base material coming out from the edges of the backing.

The amount of BPAA for serving as the active ingredient in the plaster of the present invention is preferably from 0.5 to 8% and more preferably from 2 to 6%. The amount of BPAA that is less than 0.5% is insufficient to elicit pharmacological effects of BPAA, whereas if the amount exceeds 8%, unfavorable situations arise, such as crystallizing of BPAA.

Aside from the above-described components, the adhesive base material of the present invention may contain a pharmaceutically acceptable absorption enhancer, refrigerant, preservative, bactericide, pigment and other pharmaceutically acceptable agents as desired.

Using the above-described adhesive components, the plaster of the present invention can be manufactured, for example, through the following process.

For example, SIS, the adhesive resin, the antioxidant, lanolin, and the softener are melted, mixed, and kneaded in a kneader heated to about 150° C. to obtain the adhesive base material, which is then cooled to 80 to 100° C. by air or water.

Subsequently, warm water, together with a BPAA solution (aqueous) to serve as the active ingredient solution, is added gradually to the adhesive base material under stirring. The resulting adhesive base material is spread on the liner to a predetermined thickness, and then, laminated with the backing. Then, the backing thus obtained is cut into desired size to produce the plaster of the present invention.

Alternatively, the adhesive base material may be prepared in a separate container and is stored into block forms. A required amount of the block forms is then melted at 80 to 100° C. and mixed with water and the active ingredient solution.

If the temperature of the adhesive base material exceeds 100° C. during addition of the aqueous solution of the active ingredient and water, water is brought to boiling and evaporates, and as a result, the amount of water in the plaster is significantly reduced. In comparison, if the temperature is lower than 80° C., the adhesive base material becomes so viscous that it is difficult to stir the mixture during the addition of the aqueous solution of the active ingredient. This prevents uniform dispersion of the active ingredient

EXAMPLES

The present invention will be further illustrated by the following examples. It is to be understood that the present invention is not limited to these examples. Details may be deleted, added, or substituted as it is deemed to be appropriate, so long as the pharmacological activities of the plaster of the present invention is not changed. Such changes are also covered within the technical scope of the present invention.

Examples 1 to 8

Adhesive base material with formulations shown in Tables 1 and 2 below were prepared.

A sheet of polyester film treated with silicone was used to serve as a liner, and a piece of fabric made from polyester fiber was used to serve as a backing for each adhesive base material. The amount of each adhesive base material coated was $100/m^2$.

TABLE 1

Formulations of adhesive base material containing BPAA

| Materials | Ex. 1 | Ex. 2 | Ex. 3 | Ex. 4 |
|---|---|---|---|---|
| SIS | 14.0 | 18.0 | 16.0 | 17.0 |
| Saturated alicyclic petroleum resin | 25.0 | — | — | — |
| Rosin ester resin | — | 22.0 | — | — |
| Terpene resin | — | — | 24.0 | 25.0 |
| Polybutene | — | — | 7.0 | 19.0 |
| Liquid paraffin | 13.0 | 6.0 | 17.0 | 8.0 |
| Polyethyleneglycol-400 | — | — | 10.0 | 5.0 |
| Dibutylhydroxytoluene | 1.0 | 1.0 | 1.0 | 1.0 |
| Lanolin | 24.0 | 25.0 | 10.0 | 10.0 |
| Purified water | 9.0 | 9.0 | 1.0 | 1.0 |
| Purified water (solvent for the BPAA) | 1.0 | 1.0 | 1.0 | 1.0 |

TABLE 1-continued

Formulations of adhesive base material containing BPAA

| Materials | Ex. 1 | Ex. 2 | Ex. 3 | Ex. 4 |
|---|---|---|---|---|
| Diisopropanolamine | 5.0 | 5.0 | 5.0 | 5.0 |
| Crotamiton | 2.5 | 2.5 | 2.5 | 2.5 |
| BPAA | 5.0 | 5.0 | 5.0 | 5.0 |
| l-menthol | 0.5 | 0.5 | 0.5 | 0.5 |
| Isopropyl myristate | — | 5.0 | — | — |

TABLE 2

Formulations of adhesive base material containing BPAA

| Materials | Ex. 5 | Ex. 6 | Ex. 7 | Ex. 8 |
|---|---|---|---|---|
| SIS | 16.0 | 10.0 | 30.0 | 10.0 |
| Terpene resin | 24.0 | 35.0 | 15.0 | 18.0 |
| Polybutene | 6.0 | 12.0 | 16.5 | — |
| Liquid paraffin | — | 10.5 | 5.0 | — |
| Polyethyleneglycol-400 | — | 1.0 | — | — |
| Dibutylhydroxytoluene | 1.0 | 1.0 | 1.0 | 1.0 |
| Lanolin | 25.0 | 5.0 | 10.0 | 40.0 |
| Purified water | 9.0 | 4.0 | 4.0 | 29.0 |
| Purified water (solvent for BPAA) | 1.0 | 1.0 | 1.0 | 1.0 |
| Diisopropanolamine | 10.0 | 3.0 | 5.0 | 0.5 |
| Crotamiton | 2.5 | 2.0 | 2.0 | — |
| BPAA | 5.0 | 5.0 | 5.0 | 0.5 |
| l-menthol | 0.5 | 0.5 | 0.5 | — |
| Cetyl alcohol | — | 10.0 | 5.0 | — |

Comparative Examples 1 to 4

As Comparative Examples, external plaster using water-free hot melted type adhesives base material and commercially available acrylic acid ester adhesives were prepared. Formulation for each Comparative Example is shown in Table 3 below.

TABLE 3

Formulations of adhesive base material for Comparative Examples

| Materials | Comp. 1 | Comp. 2 | Comp. 3 | Comp. 4 |
|---|---|---|---|---|
| SIS | 18.0 | 20.0 | — | — |
| Terpene resin | 29.0 | 31.0 | — | — |
| Polybutene | 15.0 | 15.0 | — | — |
| Liquid paraffin | 9.0 | 15.0 | — | — |
| Polyethyleneglycol-400 | 5.0 | 5.0 | 5.0 | 5.0 |
| Dibutylhydroxytoluene | 1.0 | 1.0 | — | — |
| Acrylic adhesive A [*1] | — | — | 72.0 | — |
| Acrylic adhesive B [*2] | — | — | — | 72.0 |
| Lanolin | 10.0 | — | 10.0 | 10.0 |
| Diisopropanolamine | 5.0 | 5.0 | 5.0 | 5.0 |
| Crotamiton | 2.5 | 2.5 | 2.5 | 2.5 |
| BPAA | 5.0 | 5.0 | 5.0 | 5.0 |
| l-menthol | 0.5 | 0.5 | 0.5 | 0.5 |

[*1] 2-ethylhexyl acrylate/vinyl acetate copolymer (commercially available)
[*2] 2-ethylhexyl acrylate/vinyl pyrrolidone copolymer (commercially available)

Test Example 1

Drug Permeability Test

Using a commercially available aqueous BPAA plaster (cataplasm) as a control, above-prepared plasters of Examples and Comparative Examples were tested for the ability to permeate the drug component in the in vitro skin permeability tests.

Methods:

Using a scalpel and scissors, a piece of abdominal skin was cut from a hairless rat and was mounted on a vertically placed Franz diffusion cell with the receptor compartment filled with saline. Warm water with a temperature of about 35° C. was circulated through the jacket of the cell.

The above-prepared plasters were each applied to the skin of hairless rat, and the receptor solution was sampled over time for each plaster The amount of the drug permeated in 24 hours was determined by HPLC.

Results:

The results of the tests are shown in Table 4. For the commercially available aqueous BPAA plaster (cataplasm) serving as the control, the amount of the permeated drug was 66.0 g/cm$^2$.

TABLE 4

Results of rat skin permeability test

| Plaster No. | Ex. 1 | Ex. 2 | Ex. 3 | Ex. 4 |
|---|---|---|---|---|
| Amount permeated μg/cm$^2$ | 58.2 | 74.6 | 62.4 | 81.5 |
| Plaster No | Ex. 5 | Ex. 6 | Ex. 7 | Ex. 8 |
| Amount permeated μg/cm$^2$ | 65.8 | 55.3 | 84.2 | 65.0 |
| Plaster No | Comp. 1 | Comp. 2 | Comp. 3 | Comp. 4 |
| Amount permeated μg/cm$^2$ | 29.8 | 21.5 | 43.7 | 31.6 |

As can be seen from the results of Table 4 above, the plaster of Examples of the present invention each exhibited higher skin permeability than the plaster of Comparative Examples. This indicates that the plaster of the present invention has an improved releasability of the drug.

Test Example 2

Stability Test

The above-prepared plasters of Examples and Comparative Examples were each placed in a polyethylene-aluminum bag, were stored for 6 months at 40° C., and were then examined for the presence of crystal deposition.

No crystal deposition was observed on the plasters of Examples, whereas crystals formed on the plasters of Comparative Examples as early as after 1 month, causing the plasters to remain stuck to the liner or significantly reducing the adhesion. No decrease was observed in the amount of the active ingredient (BPAA) in any of the preparations.

The presence or the absence of crystal deposition on the plasters observed after the storage period was shown in Tables 5 through 7, with the results of the adhesive strength of the plasters.

The adhesive strength (unit=g/25 mm) was measured by peeling the plaster from a Bakelite plate at 180° angles.

TABLE 5

Results of stability test (Examples 1 to 4)

| | | Ex. 1 | Ex. 2 | Ex. 3 | Ex. 4 |
|---|---|---|---|---|---|
| Initial (after production) | Crystal | None | None | None | None |
| | Adhesive strength | 780 | 890 | 540 | 690 |
| 40° C. 1 month | Crystal | None | None | None | None |
| | Adhesive strength | 750 | 870 | 610 | 710 |
| 40° C. 3 months | Crystal | None | None | None | None |
| | Adhesive strength | 760 | 890 | 590 | 680 |
| 40° C. 6 months | Crystal | None | None | None | None |
| | Adhesive strength | 740 | 790 | 620 | 690 |

TABLE 6

Results of stability test (Examples 5 to 8)

| | | Ex. 5 | Ex. 6 | Ex. 7 | Ex. 8 |
|---|---|---|---|---|---|
| Initial (after production) | Crystal | None | None | None | None |
| | Adhesive strength | 750 | 480 | 360 | 100 |
| 40° C. 1 month | Crystal | None | None | None | None |
| | Adhesive strength | 770 | 500 | 410 | 120 |
| 40° C. 3 months | Crystal | None | None | None | None |
| | Adhesive strength | 730 | 490 | 400 | 90 |
| 40° C. 6 months | Crystal | None | None | None | None |
| | Adhesive strength | 750 | 480 | 390 | 90 |

TABLE 7

Results of stability test (Comparative Examples 1 to 4)

| | | Comp. 1 | Comp. 2 | Comp. 3 | Comp. 4 |
|---|---|---|---|---|---|
| Initial (after production) | Crystal | None | None | None | None |
| | Adhesive strength | 2340 | 1780 | 2540 | 1520 |
| 40° C. 1 month | Crystal | formed | formed | formed | Formed |
| | Adhesive strength | 1580 | 320 | 410 | 280 |
| 40° C. 3 months | Crystal | formed | formed | formed | Formed |
| | Adhesive strength | 1460 | 380 | 340 | 250 |
| 40° C. 6 months | Crystal | formed | formed | formed | Formed |
| | Adhesive strength | 1390 | 350 | 390 | 280 |

As can be seen from the results of Tables 5 to 7, BPAA did not crystallize from the layer of the adhesive base material in any of the plaster of Examples of the present invention. Also, little change was observed in the adhesive strength in the plaster of Examples.

In contrast deposition of BPAA crystals was observed in each of the plaster of Comparative Examples. These plaster lost adhesive strength significantly over time, failing to maintain their initial adhesion strength

INDUSTRIAL APPLICABILITY

As mentioned above, the plaster for external use of the present invention, which is obtained by dissolving BPAA into an aqueous hot melted type adhesive base material comprising as essential components a styrene-isoprene-styrene block copolymer, an adhesive resin, an antioxidant, lanolin, and water, is advantageous in that it exhibits a good drug stability as well as a good drug releasability over time and the adhesion of the plaster is not decreased over time.

What is claimed is:

1. An analgesic and anti-inflammatory external plaster which comprises 0.5-8% by weight of 4-biphenylyl acetic acid (BPAA) dissolved in an aqueous hot melt type adhesive base material comprising 0-30% by weight of styrene-isoprene-styrene block copolymer, 15-35% by weight of an adhesive resin, 0.1-2% by weight of an antioxidant, 5-40% by weight of lanolin, and 0.1-30% by weight of water.

2. The analgesic and anti-inflammatory external plaster according to claim 1, wherein said aqueous hot melt type adhesive base material consists essentially of 0.5-8% by weight of 4-biphenylyl acetic acid (BPAA) dissolved in an acpueous hot melt type adhesive base material comprising 0-30% by weight of styrene-isoprene-styrene block copolymer, 15-35% by weight of adhesive resin, 0.1-2% by weight of antioxidant, 5-40% by weight of lanolin, and 0.1-30% by weight of water.

3. The analgesic and anti-inflammatory external plaster according to claim 2, wherein the amount of the water is in a range of 0.3 to 20%.

4. The analgesic and anti-inflammatory external plaster according to claim 2, further including a solubilizer for said BPAA.

5. The analgesic and anti-inflammatory external plaster according to claim 4, wherein said solubilizer is selected from the group consisting of monoethanolamine, diethanolamine, diisopropanolamine, triethanolamine, triisopropanolamine, crotamiton, and mixtures thereof.

6. The analgesic and anti-inflammatory external plaster according to claim 4, wherein said solubilizer is present in an amount of 1-15% by weight.

7. The analgesic and anti-inflammatory external plaster according to claim 2, further including a softener.

8. The analgesic and anti-inflammatory external plaster according to claim 7, wherein said softener is present in an amount of 10-45% by weight.

9. The analgesic and anti-inflammatory external plaster according to claim 2, further including a member of the group consisting of a pharmaceutically acceptable absorption enhancer, a refrigerant, a preservative, a bactericide, a pigment, and mixtures thereof.

10. The analgesic and anti-inflammatory external plaster according to claim 2, wherein said BPAA is present in an amount of 0.5-8% by weight.

11. The analgesic and anti-inflammatory external plaster according to claim 10, wherein said BPAA is present in an amount of 2-6% by weight.

12. The analgesic and anti-inflammatory external plaster according to claim 2, wherein said resin is selected from the group consisting of aromatic resins, aliphatic resins, alicyclic petroleum resins, rosin resins, rosin ester resins, and terpene resins; and said antioxidant is selected from the group consisting of dibutylhydroxytoluene, pentaerythrityltetrakis [3-(3,5-di-t-butyl-4-hydroxyphenyl)] propionate, and tocopherol acetate.

13. The analgesic and anti-inflammatory external plaster according to claim 2, wherein said lanolin is present in an amount of 10-30% by weight.

14. The analgesic and anti-inflammatory external plaster according to claim 2, wherein said resin is selected from the group consisting of alicyclic petroleum resins, rosin ester resins, and terpene resins.

15. The analgesic and anti-inflammatory external plaster according to claim 2, further comprising a softener, wherein said softener is selected from the group consisting of polybutene (liquid rubber), liquid paraffin, and isopropyl myristate (fatty acid ester); and said softener is present in an amount of 10-45% by weight.

16. The analgesic and anti-inflammatory external plaster according to claim 1, wherein said resin is selected from the group consisting of aromatic resins, aliphatic resins, alicyclic petroleum resins, rosin resins, rosin ester resins, and terpene resins; and said antioxidant is selected from the group consisting of dibutylbydroxytoluene, pentaerythrityltetrakis [3-(3,5-di-t-butyl-4-hydroxyphenyl)] propionate, and tocopherol acetate.

17. The analgesic and anti-inflammatory external plaster according to claim 1, wherein said lanolin is present in an amount of 10-30% by weight.

18. The analgesic and anti-inflammatory external plaster according to claim 1, wherein said resin is selected from the group consisting of alicyclic petroleum resins, rosin ester resins, and terpene resins.

19. The analgesic and anti-inflammatory external plaster according to claim 1, further comprising a softener, wherein said softener is selected from the group consisting of polybutene (liquid rubber), liquid paraffin, and isopropyl myristate (fatty acid ester); and said softener is present in an amount of 10-45% by weight.

20. An analgesic and anti-inflammatory external plaster containing 4-biphenylyl acetic acid (BPAA), said plaster being made by melting and kneading a styrene-isoprene-styrene block copolymer, an adhesive resin, an antioxidant, lanolin, and a softener to form an adhesive base material; adding water and an aqueous solution of BPAA to the adhesive base material at a temperature of 80 to 100° C., while stirring, to form an adhesive base material containing BPAA; coating said adhesive base material containing BPAA on a liner; attaching the liner to a base cloth; and cutting the base cloth to a desired size.

21. The analgesic and anti-inflammatory external plaster according to claim 20, wherein the amount of the water is in a range of 0.1 to 30%.

22. The analgesic and anti-inflammatory external plaster according to claim 21, wherein the amount of the water is in a range of 0.3 to 20%.

23. A process for producing an analgesic and anti-inflammatory external plaster containing 4-biphenylyl acetic acid, comprising melting and kneading a styrene-isoprene-styrene block copolymer, an adhesive resin, an antioxidant, lanolin, and a softener to form an adhesive base; adding water and an aqueous solution of BPAA to the adhesive base at a temperature of 80 to 100° C., while stirring, to form an adhesive base material containing BPAA; coating said base material on a liner; laminating the backing; and cutting the backing thus obtained into a desired size.

* * * * *